(12) United States Patent
Fink et al.

(10) Patent No.: US 7,321,796 B2
(45) Date of Patent: Jan. 22, 2008

(54) METHOD AND SYSTEM FOR TRAINING A VISUAL PROSTHESIS

(75) Inventors: Wolfgang Fink, Montrose, CA (US); Mark Humayun, Glendale, CA (US)

(73) Assignees: California Institute of Technology, Pasadena, CA (US); Doheny Eye Institute, Los Angeles, CA (US)

( * ) Notice: Subject to any disclaimer, the term of this patent is extended or adjusted under 35 U.S.C. 154(b) by 372 days.

(21) Appl. No.: 10/837,163

(22) Filed: Apr. 30, 2004

(65) Prior Publication Data

US 2004/0236389 A1 Nov. 25, 2004

Related U.S. Application Data

(60) Provisional application No. 60/467,037, filed on May 1, 2003.

(51) Int. Cl.
A61N 1/36 (2006.01)

(52) U.S. Cl. ........................................ 607/54

(58) Field of Classification Search ............ 607/2, 607/53, 54, 115, 116, 141; 623/4.1
See application file for complete search history.

(56) References Cited

U.S. PATENT DOCUMENTS

| | | | |
|---|---|---|---|
| 5,016,633 A | 5/1991 | Chow | |
| 5,024,223 A | 6/1991 | Chow | |
| 5,109,844 A | 5/1992 | de Juan, Jr. et al. | |
| 5,476,494 A | 12/1995 | Edell et al. | |
| 5,556,423 A | 9/1996 | Chow et al. | |
| 5,575,813 A | 11/1996 | Edell et al. | |
| 5,597,381 A | 1/1997 | Rizzo, III | |
| 5,767,913 A | 6/1998 | Kassatly | |
| 5,790,177 A | 8/1998 | Kassatly | |
| 5,836,996 A | 11/1998 | Doorish | |
| 5,865,839 A | 2/1999 | Doorish | |
| 5,873,901 A | 2/1999 | Wu et al. | |
| 5,895,415 A | 4/1999 | Chow et al. | |
| 5,935,155 A | 8/1999 | Humayun et al. | |
| 5,944,747 A | 8/1999 | Greenberg et al. | |
| 6,165,192 A | 12/2000 | Greenberg et al. | |
| 6,230,857 B1 | 5/2001 | Ciriello | |
| 6,324,429 B1 | 11/2001 | Shire et al. | |
| 6,389,317 B1 | 5/2002 | Chow et al. | |
| 6,393,327 B1 | 5/2002 | Scribner | |

(Continued)

OTHER PUBLICATIONS

"psycophysical test of a tunable retina encoder for retina implants" Becker et al, 1999 IEEE, pp. 192-195.*

(Continued)

*Primary Examiner*—George R. Evanisko
(74) *Attorney, Agent, or Firm*—Ropes & Gray LLP

(57) ABSTRACT

A method for training a visual prosthesis includes presenting a non-visual reference stimulus corresponding to a reference image to a visual prosthesis patient. The visual prosthesis including a plurality of electrodes. Training data sets are generated by presenting a series of stimulation patterns to the patient through the visual prosthesis. Each stimulation pattern in the series, after the first, is determined at least in part on a previous subjective patient selection of a preferred stimulation pattern among stimulation patterns previously presented in the series and a fitness function optimization algorithm. The presented stimulation patterns and the selections of the patient are stored and presented to a neural network off-line to determine a vision solution.

33 Claims, 5 Drawing Sheets

U.S. PATENT DOCUMENTS

| | | |
|---|---|---|
| 6,400,989 B1 * | 6/2002 | Eckmiller .................... 607/54 |
| 6,458,157 B1 * | 10/2002 | Suaning .................... 623/6.63 |
| 6,493,587 B1 | 12/2002 | Eckmiller et al. |
| 6,493,878 B1 | 12/2002 | Kassatly |
| 6,507,758 B1 | 1/2003 | Greenberg et al. |
| 6,530,954 B1 | 3/2003 | Eckmiller |
| 6,533,798 B2 | 3/2003 | Greenberg et al. |
| 6,611,716 B2 | 8/2003 | Chow et al. |
| 6,647,297 B2 | 11/2003 | Scribner |
| 6,668,190 B2 | 12/2003 | Iezzi et al. |
| 2001/0037061 A1 | 11/2001 | Eckmiller et al. |
| 2002/0002381 A1 | 1/2002 | Greenberg et al. |
| 2002/0038134 A1 | 3/2002 | Greenberg et al. |
| 2002/0087202 A1 | 7/2002 | Chow |
| 2002/0091421 A1 | 7/2002 | Greenberg |
| 2002/0091422 A1 | 7/2002 | Greenberg |
| 2002/0099420 A1 | 7/2002 | Chow et al. |
| 2002/0111655 A1 | 8/2002 | Scribner |
| 2002/0161417 A1 | 10/2002 | Scribner |
| 2002/0193845 A1 | 12/2002 | Greenberg et al. |
| 2003/0004546 A1 | 1/2003 | Casey |
| 2003/0014089 A1 | 1/2003 | Chow et al. |
| 2003/0028225 A1 | 2/2003 | Chow et al. |
| 2003/0055494 A1 * | 3/2003 | Bezuidenhout et al. .... 623/1.39 |
| 2003/0093132 A1 | 5/2003 | Eckmiller |
| 2003/0097165 A1 | 5/2003 | Krulevitch |
| 2003/0097166 A1 | 5/2003 | Krulevitch |
| 2003/0122954 A1 | 7/2003 | Kassatly |
| 2003/0158588 A1 | 8/2003 | Rizzo et al. |
| 2003/0181957 A1 | 9/2003 | Greenberg et al. |
| 2004/0030383 A1 * | 2/2004 | Havey et al. ................ 623/4.1 |
| 2004/0039401 A1 | 2/2004 | Chow et al. |

OTHER PUBLICATIONS

Napp-Zinn, H, et al., "Recognition and Tracking of Event Patterns with Delay-Adaption in Biology-Inspired Pulse Processing Neural Net (BPN) Hardware," Biological Cybernetics, Jun. 1, 1993.

* cited by examiner

METHOD AND SYSTEM FOR TRAINING A VISUAL PROSTHESIS

CROSS REFERENCE TO RELATED APPLICATIONS

This application claims priority to U.S. Provisional Patent Application No. 60/467,037, entitled "Blind Patient in the Loop Optimization Algorithm for Electrical Stimulation Patterns for Retinal Implants Electrode Arrays" filed on May 1, 2003, the entirety of which is hereby incorporated by reference.

FIELD OF INVENTION

The invention relates generally to visual prosthesis technology, and in one embodiment, to methods for training retinal implants.

BACKGROUND OF THE INVENTION

A healthy individual's visual perception process begins with the individual's retina(s) receiving stimulation in the form of light. The individual's nerve cells within the retina communicate a signal corresponding to the stimulation to the optic nerve. The optic nerve subsequently transmits a corresponding signal to the visual cortex through the lateral geniculate nucleus. For a vision impaired patient, visual perception may be induced by providing electrical stimulation at one or more of these locations, depending on the nature patient's given impairment.

Previous studies have shown that controlled electrical stimulation of the retina induces visual perception in blind patients. A healthy retina has over 100 million photoreceptors. Far fewer, however, are required to restore at least low resolution vision in blind individuals. For example, to enable a blind person to attain unaided mobility and large print reading, two important quality of life indicators, tests have shown that such abilities can be provided with orders of magnitude fewer photoreceptors being active. Implants, such as those developed by Second Sight, LLP of Sylmar, California, or described, for example, in U.S. Pat. No. 5,935,155 by Humayan et al. and U.S. Pat. No. 5,109,844 to De Juan, Jr. et al., which include arrays of electrodes coupled to nerve cells of a patient's retina, have been shown to be able to restore low resolution visual perception to blind patients.

While current implant technology has been demonstrated to stimulate some amount of visual perception, each implant needs to be trained for its individual patient in order to effectively elicit the appropriate visual perception. Prime candidates for the retinal implants are previously sighted individuals who have had their normal retinal nerve activity damaged by various conditions, for example macular degeneration or retinitis pigmentosa. However, due to the retinal damage in such candidates, predicting in advance the perception induced by a retinal implant in a particular candidate has proven difficult.

SUMMARY OF THE INVENTION

The invention addresses the deficiencies in the art by, in one aspect, providing a method for training a visual prosthesis (e.g., a retinal implant, a cortical implant, a lateral geniculate nucleus implant, or an optical nerve implant) to adapt to the patient in which it is implanted. According to this aspect, the method includes providing a non-visual reference stimulus to a patient having a visual prosthesis based on a reference image. The non-visual reference stimulus is intended to provide the patient an expectation of the visual image the visual prosthesis will induce. Non-visual reference stimuli include, without limitation, a pinboard, Braille text, or a verbal communication. The visual prosthesis stimulates the patient's nerve cells with a series of stimulus patterns attempting to induce a visual perception that matches the patient's expected perception derived from the non-visual reference stimulus. The patient provides feedback to indicate which of the series of stimulus patterns induces a perception that most closely resembles the expected perception. The invention employs the patient feedback as a fitness function (also referred to as a cost function or an energy function). Subsequent stimuli provided to the patient through the visual prosthesis are based, at least in part, on the previous feedback of the patient as to which stimulus pattern(s) induce the perception that best matches the expected perception. According to one embodiment, the subsequent stimulus patterns are also based, at least in part, on a fitness function optimization algorithm. In one embodiment, the fitness function optimization algorithm is a simulated annealing algorithm. In another implementation, the fitness function optimization algorithm is a genetic algorithm.

According to one feature, the invention stores the reference image and the series of stimulus patterns presented to the patient, along with the choices indicated by the patient, as a first training set. The invention may generate additional training sets using additional reference images and series of corresponding stimulus patterns. In one embodiment, the fitness function optimization is modified between the stimulation of each series of stimulation patterns. In other embodiments, the fitness function optimization algorithm is static. According to one feature, a neural network analyzes the training set offline to determine a vision solution for the visual prosthesis.

In another aspect, the invention provides a system for training a visual prosthesis such as a retinal implant, a cortical implant, a lateral geniculate nucleus implant, or an optical nerve implant. The system includes a training processor configured to generate and present series of stimulation patterns corresponding to a reference image. As in the above-described method, subsequent stimulation patterns are based, at least in part, on patient input and/or a fitness function optimization algorithm. The system includes a tool for identifying to a patient the reference image that the patient should expect to perceive using a non-visual reference stimulus. The system includes a user input for the patient to identify which of a set of stimulation patterns in each series induces a perception most closely resembling the expected perception derived from the non-visual reference stimulus.

BRIEF DESCRIPTION OF THE FIGURES

The foregoing discussion will be understood more readily from the following detailed description of the invention with reference to the following drawings.

ILLUSTRATIVE DESCRIPTION

For illustrative purposes, the methods and systems below are described with specific reference to retinal implants. The methods also apply to the training of optical nerve implants, lateral geniculate nucleus implants, and cortical implants.

Figure 1:
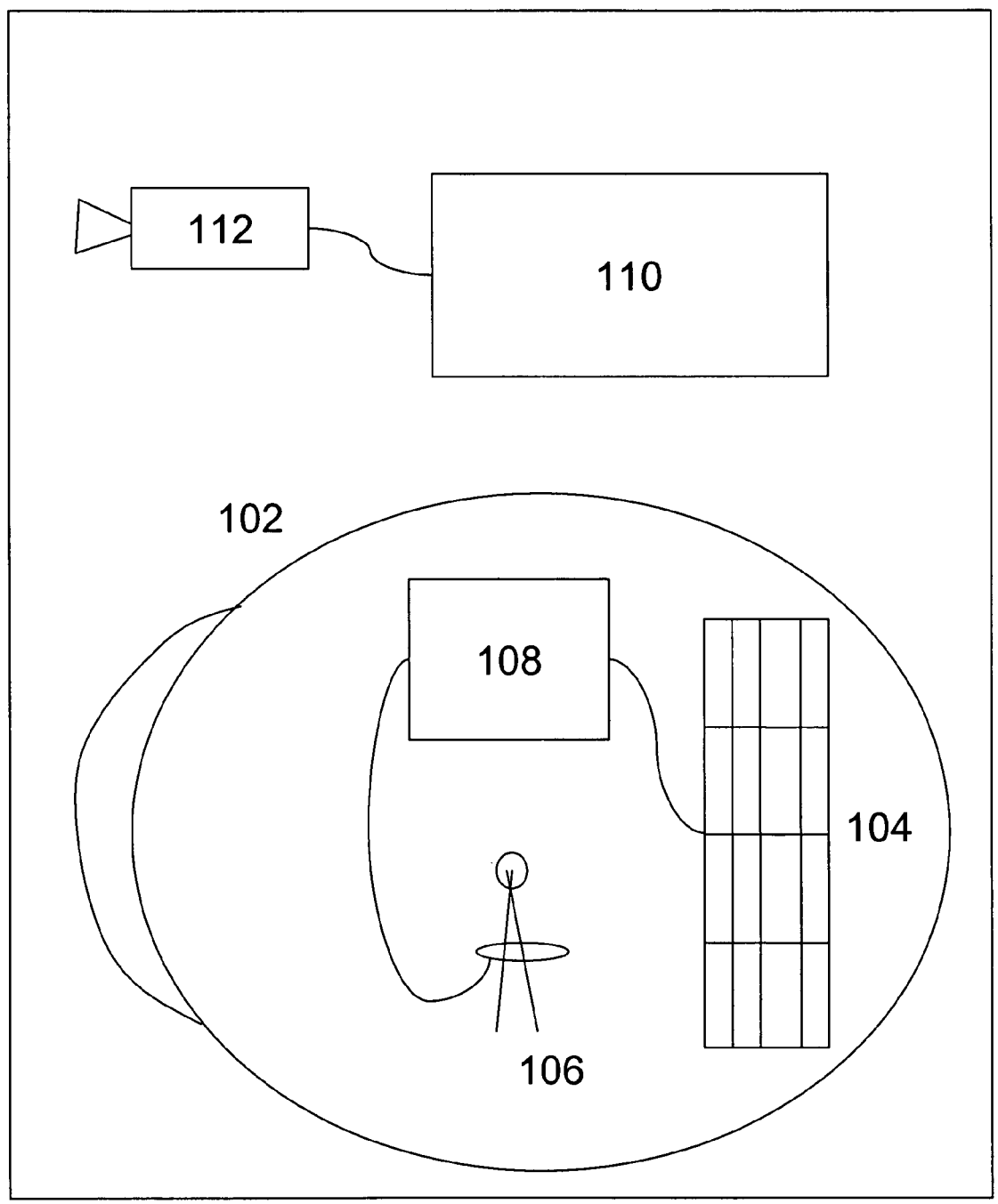
FIG. 1 is a schematic depiction of a retinal implant according to an illustrative embodiment of the invention.

FIG. 1 is a schematic depiction of a retinal implant system 100 according to one embodiment of the invention. The retinal implant system 100 includes elements implanted within a patient's eye 102 and portions exterior to the patient's eye 102. For example, in the illustrative example, the retinal implant system 100 includes an electrode array 104, a receiver 106, and an electrode array processor 108 implanted within the patient's eye 102. An image processor 110 and video camera 112 remain outside of the patient's eye. In other embodiments, the image processor 110 can be implanted within the patient's eye 110 or elsewhere within the patient. In other embodiments, the video camera 112 can be replaced with other image capture devices such as CCD arrays.

The electrode array processor 108 is electrically connected to the electrode array 104 and generates an electrical stimulus for output through each electrode in the electrode array 104. Electrode stimulation does not necessarily have a one-to-one correspondence to a patient perceiving a pixel of light. For example, in some patients, in order to induce perception of one particular pixel of vision, two or more electrodes may need to be energized. The electrode array processor 108 receives its drive instructions from the receiver 106 which in turn wirelessly receives instructions from the image processor 110.

In the illustrative embodiment, the patient wears the image processor 110, for example, on his or her belt. In addition to the image processor 110, the retinal implant system 100 includes a camera 112 for providing vision information to the image processor 110. The image processor 110 then processes the vision information to determine the appropriate electrical stimuli patterns for the retinal implant 100. The image processor 110 can be implemented in either hardware, such as, and without limitation, an ASIC, Digital Signal Processor, or other integrated circuit, or in software operating on a computing device, or in a combination of the two.

In one embodiment, the image processor 110 receives a digital image from the video camera 112. The image processor 110 converts the received image to a gray scale and reduces/downscales the resolution of the image to a resolution matching the number of electrodes in the electrode array 104. In other embodiments, the image processor 110 retains the image in color. The image processor 110 then determines the appropriate electrical stimulus for each electrode in the electrode array 104 based on a vision solution. The vision solution determines the values of a number of parameters that can be manipulated for each electrode, including, without limitation, for example, the amplitude of the voltage applied to each electrode (if any), the timing of the onset of the electrical signal applied to each electrode relative to the other electrodes, the shape of the signal applied to each electrode, the width of a pulse applied to the electrode, the frequency of the signal applied, and the duration of the voltage applied to the electrode. In contrast to methods of training optical implants that tune temporal-spatial filters to model a healthy retina, the illustrative training method determines direct electrode outputs in response to received images.

The image processor 110, after generating a stimulus pattern for the electrode array 104, transmits the stimulus pattern wirelessly to the receiver 106 within the patient's eye 102.

Figure 2:
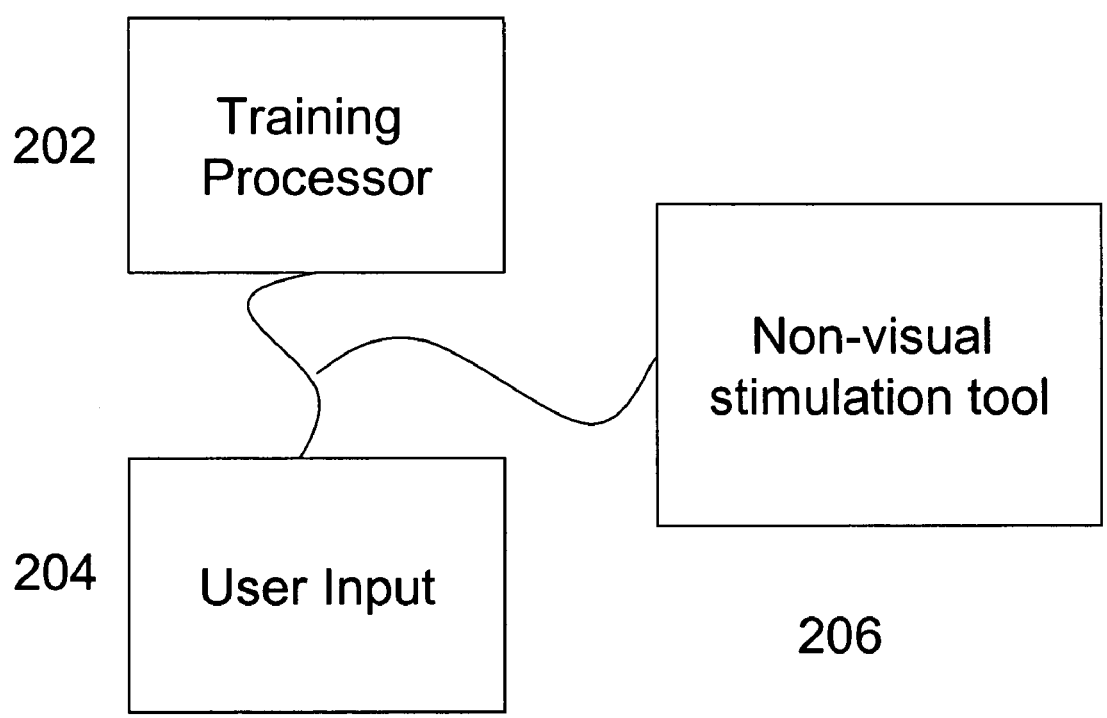
FIG. 2 is a block diagram of a system for retinal implant training according to an illustrative embodiment of the invention.

FIG. 2 is a conceptual high-level block diagram of a retinal implant training system 200. The training system 200 includes a training processor 202, a user input 204, and a reference image identification tool 206. The elements of the training system 200 will be best understood with reference to the method described in FIG. 3.

Figure 3:
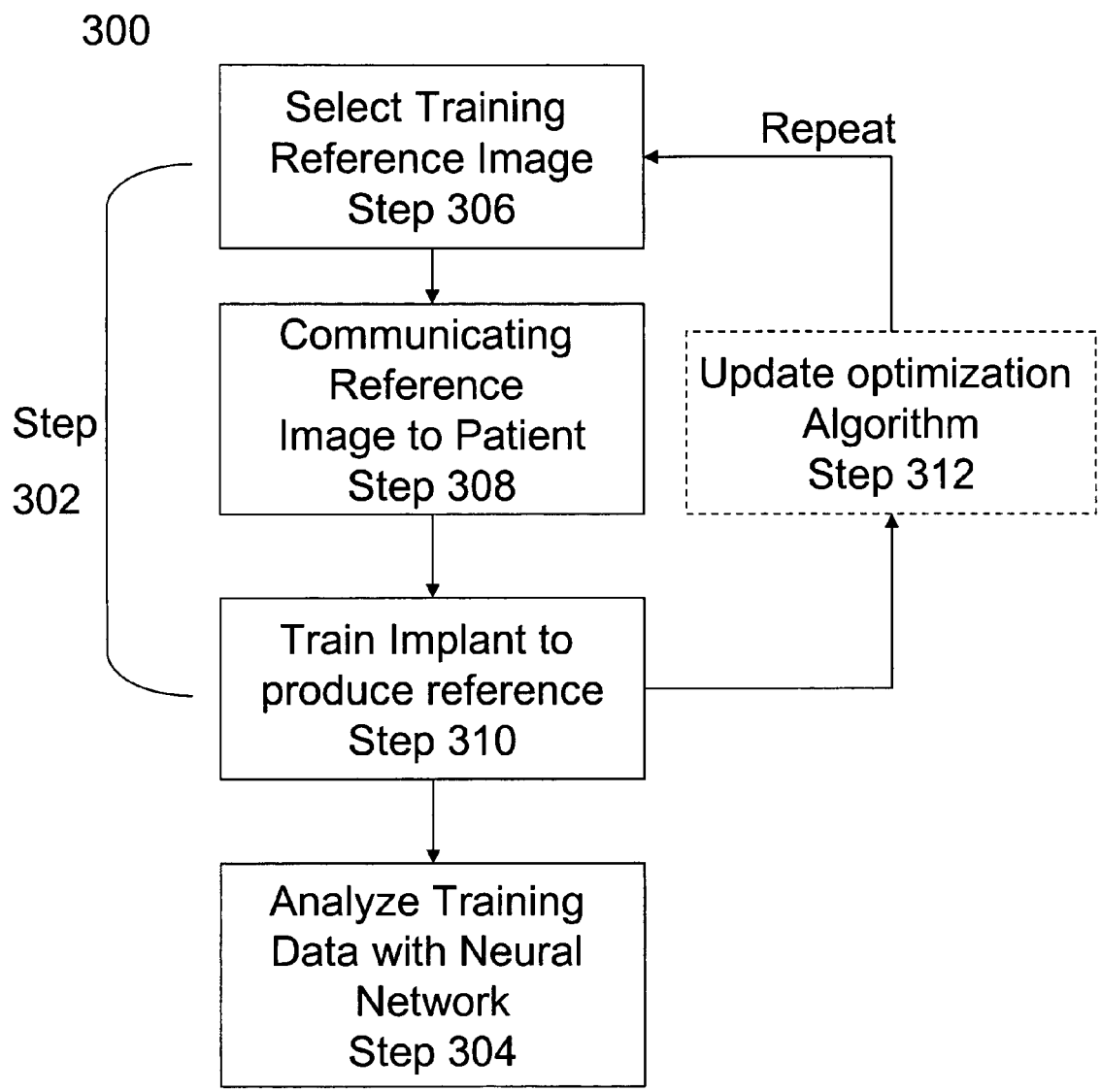
FIG. 3 is a flowchart of a method of training a retinal implant according to an illustrative embodiment of the invention.

FIG. 3 is a flowchart of a method 300 for training a retinal implant 100, such as the implant described in FIG. 1, to determine a vision solution for an individual patient's retinal implant 100. A patient participates in training his or her individual implant 100 with the aid of the training system 200. In general, the training method 300 can be divided into two portions, generating training data (step 302) and processing training data (step 304) to produce the vision solution.

Generating training data (step 302) can be further divided into three processes: i) selecting a training reference image (step 306), ii) communicating the reference image to the patient (step 308), and iii) training the patient's implant to successfully produce the reference image (step 310).

First, the training processor 202 selects a first training reference image (step 306) to attempt to stimulate perception of in the patient. In one embodiment the training reference image is selected from a predefined group, such as letters, numbers, or basic shapes. For example, the first training reference image may be a solid white rectangle. Subsequent training reference images include individual straight vertical and horizontal lines at the extremities of the patient's inducible field-of-view. Other preliminary training reference images include individual bright spots at various locations in a patient's field of view. The training set then identifies the first training reference image to the patient using a non-visual reference stimulus (step 308), for example by employing the reference image identification tool 206. The non-visual reference stimulus provides the patient an expectation of the perception the implant 100 is attempting to induce.

Figure 4:
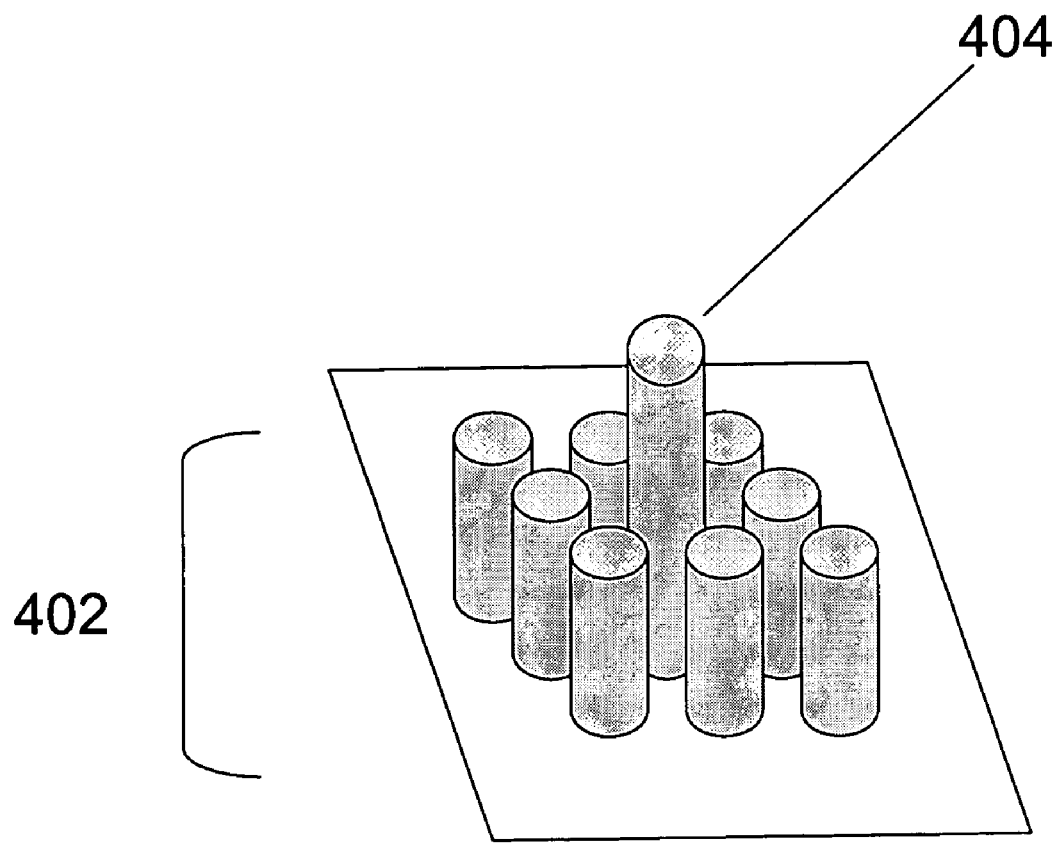
FIG. 4 is an illustrative non-visual reference identification tool according to an illustrative embodiment of the invention.

FIG. 4 is an example 400 of a reference image identification tool 206. The tool 400 includes an array 402 of pins (e.g., 404) whose positions relative to one another can be rearranged to form a physical relief corresponding to the reference image. The array 402 generally has one pin 404 per pixel of resolution of the reference image. For example, the configuration of the pins of the tool 400 corresponds to a reference image having a simple single bright spot in the center of the patient's field-of-view. The training processor 202 controls the arrangement of the pins 404 in the array 402. Other deformable tools can be similarly employed to provide a tactile stimulus representing the first training reference image. Alternatively, if the patient previously had been sighted, the patient can be informed of the first training reference image verbally. In such embodiments, the tool for non-visually communicating the reference image can be a person, for example a doctor aiding in the training, or an audio speaker connected to a speech synthesizer. In another embodiment, the training system 200 can identify the reference image using Braille text.

Referring back to FIGS. 2 and 3, the training system 200 then trains the implant 100 to correctly induce perception of the reference image (step 310).

Figure 5:
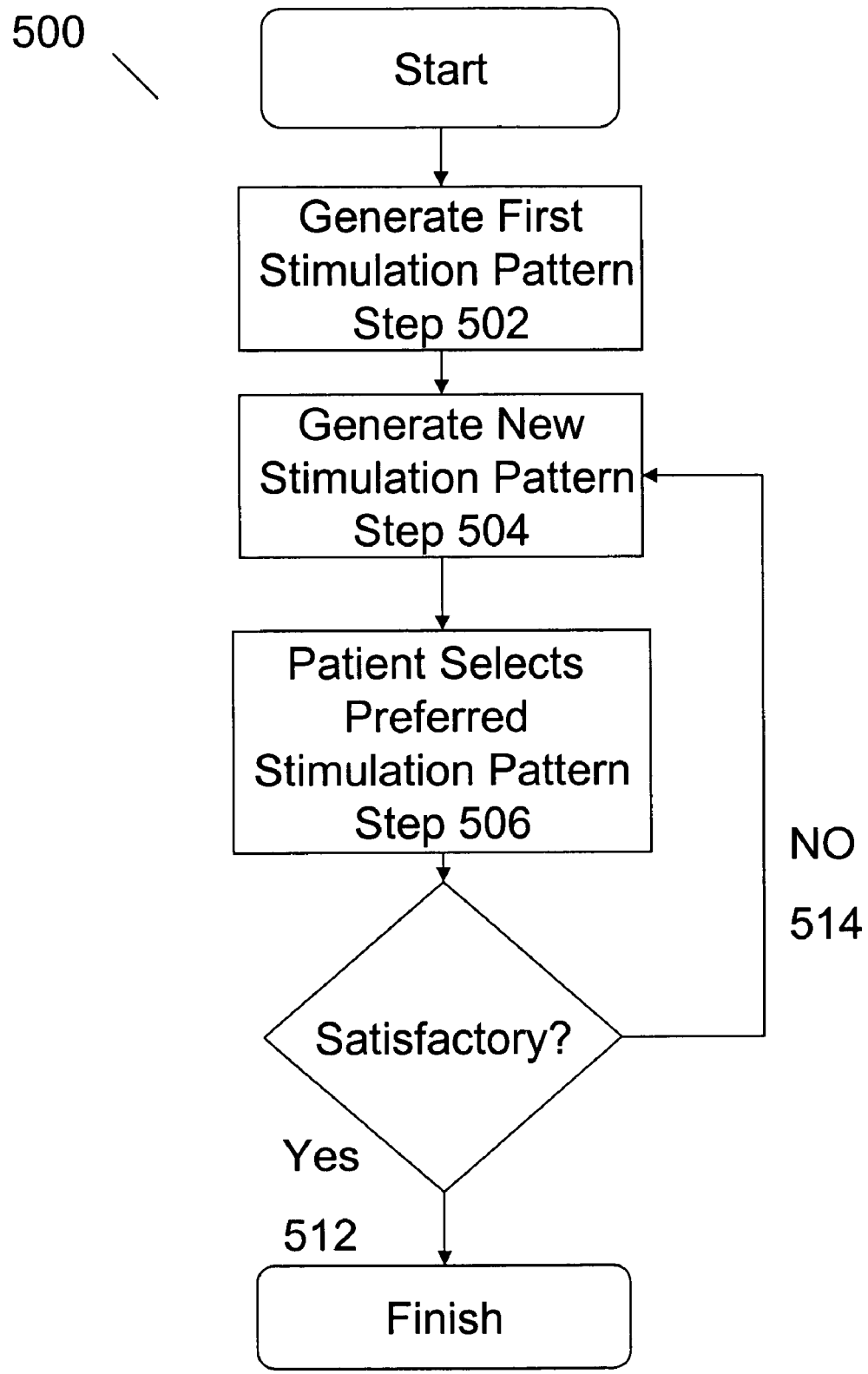
FIG. 5 is a flowchart of a method for generating training data sets for training a retinal implant according to an illustrative embodiment of the invention.

FIG. 5 is a flow chart of a method 500 for training the retinal implant to induce perception of a reference image, according to an illustrative embodiment of the invention. The training processor 202 communicates a first stimulation pattern to the retinal implant (step 502) by transmitting instructions to the electrode array processor 108. Subsequently, the training processor 202 generates a second stimulation pattern (step 504). The electrode processor 108 energizes the electrodes 104 according to the stimulation patterns. The patient, perceiving the results induced by the stimulation patterns, and having an expectation of the induced perception based on the non-visual reference stimulus, selects, using the input 204, the stimulation pattern that induces a visual perception closest to the expected perception (step 506). Based on the selection by the patient and preferably a fitness function optimization algorithm, the training system 200 generates yet another stimulation pattern (step 504). The patient chooses between the previously selected stimulation pattern and the most recently generated stimulation pattern, once again, based on which stimulation pattern induces the visual perception most closely matching the expected perception (step 506). This process continues until the generated stimulation pattern induces a visual perception that sufficiently matches the expectations of the patient (step 512).

In practice, no stimulation pattern may generate a perception that identically matches the patient's expected perception of the training reference image. According to one feature, the training processor 202 generates new stimulation patterns until the patient recognizes diminishing returns in each new stimulation pattern. At that point, the patient chooses the best available fit.

As indicated above, the generation of each stimulation pattern after the first is based at least in part on a fitness function optimization algorithm. In one embodiment, the fitness function optimization algorithm is a simulated-annealing algorithm. Simulated annealing is a widely used and well-established optimization technique, particularly suited for high-dimensional configuration spaces. The goal of the algorithm is to minimize an energy function, in this case, the subjective evaluation by the blind patient of the difference between the perceived image and the expected perception.

The minimization is performed by randomly changing the value of one or more of the stimulation parameters within physiologically tolerable limits and reevaluating the energy function. Two cases can occur: 1) the change in the variable values results in a new, lower energy function value, i.e. the patient prefers the changed stimulation pattern; or 2) the energy function value is higher or unchanged, i.e. the patient prefers the prior stimulation pattern or has no opinion on which pattern is better. In the first scenario, the new set of parameter values is stored and the change accepted. In the second scenario, the new set of variable values is only stored with a certain likelihood (Boltzmann probability, including an annealing temperature). This ensures that the overall optimization algorithm does not get stuck in local minima of the energy function too easily. The annealing temperature directly influences the Boltzmann probability by making it less likely to accept an energetically unfavorable step, the longer the optimization lasts (cooling schedule). Then, the overall procedure is repeated until the annealing temperature has reached its end value or a preset number of iterations has been exceeded.

In one embodiment, the training system 200 applies a derivative of the canonical simulated annealing algorithm, by replacing the Boltzmann probability acceptance with an energy threshold acceptance: each configuration with an energy E<Emin+Ethreshold will be automatically accepted, with Ethreshold oscillating between to preset boundaries similar to "simulated reheating and cooling".

In another embodiment, the fitness function optimization algorithm is a genetic algorithm. In general, genetic algorithms try to mimic evolutionary principles used by nature in applying genetic operations such as point mutation, crossover, and inversion to parameter strings, called "genes" or "chromosomes", in order to "evolve" a set of parameters that achieves a high fitness as determined by a fitness function (similar to the energy function in simulated annealing).

In one such embodiment, the training system 200 uses the following genetic algorithm to generate stimulation patterns. The training system 200 begins with generating a stimulation pattern having a set of parameters having random values within physiologically tolerable limits. The training system 200 replaces patient rejected stimulation patterns with stimulation patterns generated by executing genetic operations on a randomly selected set of the stimulation pattern parameters.

In another embodiment, the algorithm operates in the following fashion. The training system 200, after receiving input from a patient compares the most recently selected stimulation pattern with the most recently rejected stimulation pattern to identify differences in electrode output parameters in the stimulation patterns. In the subsequently generated stimulation pattern, at least one identified difference between the stimulation patterns is further emphasized. For example, if the voltage applied to a particular electrode in the electrode array in the selected stimulation pattern is 5% greater than the voltage applied to that electrode in the rejected stimulation pattern, a subsequent stimulation pattern would apply a voltage to that electrode that is 8% greater than that applied in the rejected stimulation pattern. Such increases in voltage to that electrode in subsequently generated stimulation patterns continue until the patient rejects the newest stimulation pattern or the voltage reaches physiologically tolerable limits. Then, a different stimulation parameter is altered in subsequently generated stimulation patterns.

After the training system 200 successfully generates a stimulation pattern that induces the visual perception expected by the patient based on the non-visual reference stimulus, the training system 200 repeats (step 514) the training process 500 with additional training reference images. The training system 200 stores training data sets including the reference image, records of all the stimulation patterns that were generated, which stimulation patterns were compared to each other, which of those patterns were selected, and the final successful stimulation patterns.

In one embodiment, the training system 200 analyzes training sets between training sessions that use different reference images in order to further optimize (step 312) the fitness function optimization algorithm. An ordered choice of reference images can facilitate this optimization (step 312).

After successful stimulation patterns for one or more training reference images are achieved, the training data set(s) is analyzed (step 304) by, for example, an artificial feed-forward-type multi-layer neural network configured, e.g., using the Error-Backpropagation algorithm; a Hopfield-type Attractor neural network configured with, e.g., the Projection Rule or the Pseudoinverse algorithm;

and/or a recurrent neural network trained, e.g., with algorithms such as Real-Time Recurrent Learning algorithm and the Time-Dependent Recurrent Backpropagation to determine a vision solution. The neural network analysis yields the vision solution, which, in one embodiment, is itself a neural network. The vision solution provides the capability to generate stimulation patterns for correctly inducting perception of the reference images and of images not presented as part of the training by applying the "knowledge" extracted from the analysis of the training data set(s). The resulting vision solution is transferred to the image processor 110.

The fitness function optimization algorithm employed by the training system 200 can further be optimized by testing the optimization algorithm on sighted subjects. Instead of communicating a reference stimulus to the sighted subject non-visually, the sighted subject is presented with the reference image along with two potential images that correspond at least in part to the reference image. As with the training of the retinal implant, the sighted subject selects the image most closely resembling the reference image. A next set of images is selected for presentation using the fitness function optimization algorithm, however, the electrical stimulus parameters are substituted with direct visual parameters such as brightness and contrast. Optimization algorithms are objectively compared by comparing the average number of iteration steps before a presented image suitably resembles the reference image.

The invention may be embodied in other specific forms without departing form the spirit or essential characteristics thereof. The forgoing embodiments are therefore to be considered in all respects illustrative, rather than limiting of the invention.

What is claimed:

1. A method for training a visual prosthesis comprising:
   presenting a non-visual reference stimulus corresponding to a reference image to a patient having a visual prosthesis, the visual prosthesis including a plurality of electrodes;
   generating a training data set by presenting a series of stimulation patterns to the patient through the visual prosthesis and receiving a corresponding series of subjective patient selections of a preferred stimulation pattern among stimulation patterns in the series of stimulation patterns previously presented to the patient until the patient identifies a successful stimulation pattern, and storing the presented stimulation patterns and the received selections of the patient;
   wherein at least one stimulation pattern in the series of stimulation patterns is determined at least in part based on a fitness function optimization algorithm and at least one previously received subjective patient selection in the series of subjective patient selections; and
   after identifying the successful stimulation pattern, presenting off-line to a neural network at least the reference image and the successful stimulation pattern from the training data set to determine a vision solution.

2. The method of claim 1 wherein the retinal prosthesis is a retinal implant.

3. The method of claim 1 further comprising:
   generating additional training data sets based on additional reference images; and
   presenting off-line to the neural network at least reference images and successful stimulation patterns from the additional training data sets.

4. The method of claim 3, comprising utilizing a same fitness function optimization algorithm for determining each series of stimulation patterns corresponding to each given reference image.

5. The method of claim 3, comprising changing the fitness function optimization algorithm between presentation of each series of stimulation patterns corresponding to different reference images.

6. The method of claim 1, comprising utilizing a simulated annealing algorithm as the fitness function optimization algorithm.

7. The method of claim 1, comprising utilizing a genetic algorithm as the fitness function optimization algorithm.

8. The method of claim 1, comprising applying the fitness function optimization algorithm to determine a subsequent stimulation pattern in the series.

9. The method of claim 1, comprising, subsequent to the off-line presentation to the neural network, providing the neural network to the patient to control the visual prosthesis.

10. The method of claim 1, wherein the successful stimulation pattern comprises a stimulation pattern that generates a patient perception that matches the reference image.

11. The method of claim 1, wherein the successful stimulation pattern comprises a stimulation pattern that the patient determines to be a best fit to the reference image.

12. A system for training a visual prosthesis comprising:
   a) a processor configured to
      i) present a non-visual reference stimulus corresponding to a reference image to a patient having a visual prosthesis via a non-visual stimulus tool, the visual prosthesis including a plurality of electrodes;
      ii) generate a training data set by presenting a series of stimulation patterns to the patient through the visual prosthesis and receiving a corresponding series of subjective selections of a preferred stimulation pattern among stimulation patterns in the series of stimulation patterns previously presented to the patient until the patient identifies a successful stimulation pattern, and storing the presented stimulation patterns and the selections of the patient, wherein at least one stimulation pattern in the series of stimulation patterns is determined at least in part based on a fitness function optimization algorithm and at least one previously received subjective patient selection in the series of subjective patient selections; and
      iii) after identifying the successful stimulation pattern, present off-line to a neural network at least the reference image and the successful stimulation pattern from the training data set to determine a vision solution; and
   b) a user input for selecting between the presented stimulation patterns.

13. The system of claim 12 wherein the processor is configured to present the series of stimulation patterns to the patient through a retinal implant.

14. The system of claim 12 wherein the processor is further configured to:
   generate additional training data sets based on additional reference images; and
   present off-line to the neural network at least reference images and successful stimulation patterns from the additional training data sets.

15. The system of claim 14 wherein the processor is configured to utilize a same fitness function optimization algorithm for determining each series of stimulation patterns corresponding to each given reference image.

16. The system of claim 14, wherein the processor is configured to changing the fitness function optimization algorithm between presentation of each series of stimulation patterns corresponding to different reference images.

17. The system of claim 12, wherein the processor is configured to utilize a simulated annealing algorithm as the fitness function optimization algorithm.

18. The system of claim 12, wherein the processor is configured to utilize a genetic algorithm as the fitness function optimization algorithm.

19. The system of claim 12, wherein the processor is configured to apply the fitness function optimization algorithm to determine a subsequent stimulation pattern in the series.

20. The system of claim 12, comprising the non-visual stimulus tool.

21. The system of claim 20, wherein the non-visual stimulus tool comprises a plurality of pins.

22. The system of claim 21, wherein the pins of the non-visual stimulus tool are configurable to correspond to respective pixels of the reference image.

23. The system of claim 20, wherein the non-visual stimulus tool comprises an audio output.

24. The system of claim 12, wherein the processor is configured to, subsequent to the off-line presentation of the reference image and successful stimulation pattern from the training data set to the neural network, providing the neural network to the patient to control the visual prosthesis.

25. The system of claim 12, wherein the processor is configured to, subsequent to the off-line presentation to the neural network, provide the neural network to the patient to control the visual prosthesis.

26. The system of claim 12, wherein the successful stimulation pattern comprises a stimulation pattern that generates a patient perception that matches the reference image.

27. The system of claim 12, wherein the successful stimulation pattern comprises a stimulation pattern that the patient determines to be a best fit to the reference image.

28. A method for training a retinal implant comprising:
presenting a non-visual reference stimulus corresponding to a reference image to a patient having a retinal implant, the retinal implant including a plurality of electrodes;
generating a training data set by presenting a series of stimulation patterns to the patient through the retinal implant and receiving a corresponding series of subjective patient selections of a preferred stimulation pattern among stimulation patterns in the series of stimulation patterns previously presented to the patient until the patient identifies a successful stimulation pattern, each stimulation pattern in the series after a first stimulation pattern in the series being determined based at least in part on a fitness function optimization algorithm and a previous subjective patient selection of a preferred stimulation pattern among stimulation patterns previously presented, and storing the presented stimulation patterns and the selections of the patient; and
after identification of the successful stimulation pattern, presenting off-line to a neural network the training data set to determine a vision solution.

29. The method of claim 28, wherein the successful stimulation pattern comprises a stimulation pattern that generates a patient perception that matches the reference image.

30. The method of claim 28, wherein the successful stimulation pattern comprises a stimulation pattern that the patient determines to be a best fit to the reference image.

31. A computer readable medium encoding instructions for causing a computer to carry out a method comprising:
presenting a non-visual reference stimulus corresponding to a reference image to a patient having a visual prosthesis, the visual prosthesis including a plurality of electrodes;
generating a training data set by (i) presenting a series of stimulation patterns to the patient through the visual prosthesis and receiving a corresponding series of subjective selections of a preferred stimulation pattern among stimulation patterns in the series of stimulation patterns previously presented to the patient until the patient identifies a successful stimulation pattern, and storing the presented stimulation patterns and the received selections of the patient;
wherein at least one stimulation pattern in the series of stimulation patterns is determined at least in part based on a fitness function optimization algorithm and at least one previously received subjective patient selection in the series of subjective patient selections; and
presenting off-line to a neural network at least the reference image and the successful stimulation pattern from training data set to determine a vision solution.

32. The computer readable medium of claim 31, wherein the successful stimulation pattern comprises a stimulation pattern that generates a patient perception that matches the reference image.

33. The computer readable medium of claim 31, wherein the successful stimulation pattern comprises a stimulation pattern that the patient determines to be a best fit to the reference image.

* * * * *